United States Patent
Ogawa et al.

(10) Patent No.: US 10,538,793 B2
(45) Date of Patent: Jan. 21, 2020

(54) ω3 FATTY-ACID DESATURASE AND METHOD FOR PRODUCING EICOSAPENTAENOIC ACID

(71) Applicants: KYOTO UNIVERSITY, Kyoto-shi (JP); NISSHIN PHARMA INC., Chiyoda-ku (JP)

(72) Inventors: Jun Ogawa, Kita-ku (JP); Akinori Ando, Sakyo-ku (JP); Eiji Sakuradani, Muko (JP); Sakayu Shimizu, Ukyo-ku (JP); Shigeru Hiramoto, Fujimino (JP); Masataka Harata, Ueda (JP); Yuki Takemoto, Fujimino (JP)

(73) Assignees: KYOTO UNIVERSITY, Kyoto-shi (JP); NISSHIN PHARMA INC., Chiyoda-ku (JP)

( * ) Notice: Subject to any disclaimer, the term of this patent is extended or adjusted under 35 U.S.C. 154(b) by 12 days.

(21) Appl. No.: 15/539,555

(22) PCT Filed: Dec. 24, 2015

(86) PCT No.: PCT/JP2015/086035
§ 371 (c)(1),
(2) Date: Jun. 23, 2017

(87) PCT Pub. No.: WO2016/104607
PCT Pub. Date: Jun. 30, 2016

(65) Prior Publication Data
US 2017/0369909 A1   Dec. 28, 2017

(30) Foreign Application Priority Data
Dec. 25, 2014 (JP) ................. 2014-262066

(51) Int. Cl.
C12N 9/02 (2006.01)
C12N 15/31 (2006.01)
C12N 15/53 (2006.01)
C12P 7/64 (2006.01)

(52) U.S. Cl.
CPC .......... *C12P 7/6427* (2013.01); *C12N 9/0071* (2013.01); *C12Y 114/19* (2013.01)

(58) Field of Classification Search
None
See application file for complete search history.

(56) References Cited

U.S. PATENT DOCUMENTS

| 5,401,646 A | 3/1995 | Shinmen et al. |
| 2003/0196217 A1 | 10/2003 | Mukerji et al. |
| 2007/0249026 A1* | 10/2007 | Xue ............... C12N 9/0083 435/134 |
| 2008/0032335 A1 | 2/2008 | Shimizu et al. |
| 2008/0125326 A1 | 5/2008 | Yadav et al. |
| 2016/0208297 A1 | 7/2016 | Ogawa et al. |

FOREIGN PATENT DOCUMENTS

| JP | 63-14697 A | 1/1988 |
| JP | 11-243981 A | 9/1999 |
| JP | 2005-515776 A | 6/2005 |
| JP | 2006-55104 A | 3/2006 |
| JP | 2007-37415 A | 2/2007 |
| JP | 2009-534032 A | 9/2009 |
| JP | 2009-534032 A5 | 9/2009 |
| JP | 2010-508019 A | 3/2010 |
| JP | 2010-508019 A5 | 3/2010 |
| JP | 2014-45740 A | 3/2014 |
| WO | WO 2015/029966 | 3/2015 |

OTHER PUBLICATIONS

Merriam-Webster online dictionary definition of "represent", last viewed on Sep. 27, 2018, 2 pages (Year: 2018).*
Ando et al., "Establishment of Agrobacterium tumefaciens-Mediated Transformation of an Oleaginous Fungus, *Mortierella alpina* 1S-4, and Its Application for Eicosapentaenoic Acid Producer Breeding", Appl. Environ. Microbiol. 75:5529-5535, 2009 (Year: 2009).*
Sang, H., Mechanisms of Development 121:1179-1186, 2004 (Year: 2004).*
Drechsler, C., J. Agri. Res. 34:287-296, 1927 (Year: 1927).*
International Search Report dated Feb. 5, 2016, in PCT/JP2015/086035 filed Dec. 24, 2015.
Shimizu et al., "Conversion of linseed oil to an eicosapentaenoic acid-containing oil by Mortierella alpina 1S-4 at low temperature", Appl Microbiol Biotechnol, vol. 32, (1989), pp. 1-4.
Nakatsuji et al., "Eicosapentaenoic acid (EPA) production by Mortierella alpine 1S-4 overexpressing omega-3 desaturase gene derived from *Pythium* sp. Under room temperature", Society for Biotechnology, (2014), with Partial Translation, 3 pages.

* cited by examiner

*Primary Examiner* — David Steadman
(74) *Attorney, Agent, or Firm* — Oblon, McClelland, Maier & Neustadt, L.L.P.

(57) ABSTRACT

Provided is ω3 desaturase having high enzymatic activity even at normal temperature. A polypeptide which consists of an amino acid sequence having an identity of 80% or more with the amino acid sequence represented by SEQ ID NO: 2 and has ω3 desaturation activity on C20 fatty acid, and a gene thereof.

11 Claims, 3 Drawing Sheets
Specification includes a Sequence Listing.

ω3 FATTY-ACID DESATURASE AND METHOD FOR PRODUCING EICOSAPENTAENOIC ACID

TECHNICAL FIELD

The present invention relates to a novel polypeptide having ω3 desaturase activity, a gene encoding the polypeptide, and use of these for producing eicosapentaenoic acid.

BACKGROUND ART

A highly-unsaturated fatty acid is a fatty acid having two or more unsaturated bonds and includes ω6 unsaturated fatty acids such as linoleic acid (LA, 18: 2n–6), γ-linolenic acid (GLA, 18: 3n–6) and arachidonic acid (ARA, 20: 4n–6); and ω3 unsaturated fatty acids such as α-linolenic acid (ALA, 18: 3n–3), eicosatetraenoic acid (ETA, 20: 4n–3), eicosapentaenoic acid (EPA, 20: 5n–3) and docosahexaenoic acid (DHA, 22: 6n–3). The highly-unsaturated fatty acids are not only involved in regulating fluidity of membrane as a major constituent of biological membrane but also important as a precursor of a biofunctional component. ARA and EPA serve as precursors of e.g., prostaglandin, thromboxane and leukotriene in higher animals; whereas DHA is a highly-unsaturated fatty acid present most abundantly in the brain. EPA has physiological effects, such as a platelet aggregation inhibitory effect, a blood triglyceride lowering effect, an anti-arteriosclerotic effect, a blood viscosity-lowering effect, a blood pressure-lowering effect, an anti-inflammatory effect, an anti-tumor effect and used in various fields including pharmaceuticals, foods, cosmetics and animal feeds. Recently, in view of lifestyle-related disease prevention, active intake of ω3 unsaturated fatty acids is recommended. Likewise, ω3 unsaturated fatty acids are lipid molecular species significantly increased in demand.

DHA and EPA of living bodies are not only taken from food but also biosynthesized from ALA in some organisms. However, since ALA cannot be biosynthesized in humans, DHA and EPA are nutritionally essential fatty acids for humans. EPA is abundantly contained mainly in oils of fish such as cod, herring, mackerel, salmon, sardine and krill; psychrotrophic marine bacteria such as *Shewanella livingstonensis*; and algae such as Labyrinthulomycetes. Methods for extracting or purifying EPA from these biological resources have been known. The most common method is purification of EPA from fish oil. However, the EPA content in fish oil is low. In addition to this problem, depending upon the extraction or purification method, fish odor sometimes remains in EPA derived from fish oil, and the content of erucic acid, which is said as a cause a heart disease, increases.

Recently, oleaginous microorganisms accumulating lipid within cells, have drawn attention in connection with energy problems and methods for microbiologically producing various types of lipids have been developed. For example, studies on a method for producing a highly-unsaturated fatty acid using microorganisms of a filamentous fungus belonging to the genus *Mortierella* have been conducted. *Mortierella* microorganisms are known to have an ω3 or ω6 highly unsaturated fatty acid metabolic pathway to produce EPA (Non Patent Literature 1). Patent Literature 1 discloses a method for producing EPA by culturing an EPA-producing *Mortierella* microorganism. Patent Literature 2 discloses a method for producing ARA and EPA using a mutant strain obtained by subjecting *Mortierella alpina* to a mutation treatment. Patent Literature 3 discloses a method for producing a highly-unsaturated fatty acid such as EPA by using a transformed strain obtained by introducing a gene encoding an ω3 unsaturated polypeptide isolated from *Mortierella alpina* into a yeast.

However, the ω3 desaturase of a *Mortierella* microorganism has a low optimum temperature and does not sufficiently function at normal temperature (about 20° C.) where the microorganism easily proliferates. For the reason, even if the *Mortierella* microorganism is cultured at normal culture temperature, EPA cannot be efficiently produced. In addition, since the ω3 desaturase of the *Mortierella* microorganism preferentially acts on a fatty acid having 18 carbon atoms, it was difficult to efficiently produce EPA having 20 carbon atoms by the conventional method using the *Mortierella* microorganism.

In the circumstances, it has been desired to develop an ω3 desaturase capable of efficiently synthesizing EPA from a fatty acid having 20 carbon atoms (e.g., ARA). An ω3 desaturase isolated from *Saprolegnia diclina* is disclosed in Patent Literature 4; Δ17 desaturase isolated from *Phytophthora ramorum* in Patent Literature 5; and Δ17 desaturase isolated from *Pythium aphanidermatum* in Patent Literature 6.

CITATION LIST

Patent Literatures

[Patent Literature 1] JP-A-63-14697
[Patent Literature 2] JP-A-11-243981
[Patent Literature 3] JP-A-2006-055104
[Patent Literature 4] JP-A-2005-515776
[Patent Literature 5] JP-A-2009-534032
[Patent Literature 6] JP-A-2010-508019

Non Patent Literature

[Non Patent Literature 1] Appl. Microbiol. Biotechnol., 1989, 32: 1-4

SUMMARY OF INVENTION

Technical Problem

The present invention relates to providing an ω3 desaturase having a high enzymatic activity even at normal temperature of 20° C. or more and an oleaginous cell having the ω3 desaturase and capable of producing a fat and oil containing ω3 unsaturated fatty acids such as EPA effectively in a high concentration. The present invention further relates to providing industrial production means for an EPA-rich fat and oil using the oleaginous cell.

Solution to Problem

The present inventors conducted various investigations. As a result, they found a novel ω3 desaturase having a high ω3 desaturation activity on a C20 fatty acid even at normal temperature and a gene encoding the ω3 desaturase. The present inventors further found that productivity of C20 ω3 unsaturated fatty acids such as EPA at normal temperature is improved in a transformed cell having the gene encoding the ω3 desaturase introduced therein.

More specifically, the present invention provides a polypeptide which consists of an amino acid sequence having an identity of 80% or more with the amino acid sequence represented by SEQ ID NO: 2 and has ω3 desaturation activity on a C20 fatty acid.

The present invention also provides a polynucleotide encoding the polypeptide.

The present invention also provides a vector comprising the polynucleotide.

The present invention also provides a transformed cell having the polynucleotide introduced therein.

The present invention also provides a method for producing an eicosapentaenoic acid-containing lipid, comprising culturing a cell expressing the polypeptide.

The present invention also provides a method for producing eicosapentaenoic acid, comprising purifying the eicosapentaenoic acid-containing lipid produced by the aforementioned method.

Advantageous Effects of Invention

The ω3 desaturase of the present invention has a high ω3 desaturation activity on a C20 fatty acid at normal temperature of 20° C. or more where cells easily proliferate and plays a role in biological synthesis of a C20 ω3 unsaturated fatty acid such as EPA. Thus, if a cell expressing the ω3 desaturase of the present invention is cultured, a C20 ω3 unsaturated fatty acid such as EPA can be efficiently produced within the cells. Since EPA is an important highly-unsaturated fatty acid to be used in various fields including pharmaceuticals, foods, cosmetics and animal feeds, the present invention applicable to industrial-scale production of EPA is extremely useful in these fields.

BRIEF DESCRIPTION OF DRAWINGS

FIG. 3A: Production amounts (mg) of individual fatty acids per culture solution (1 mL), FIG. 3B: Production amounts (mg) of individual fatty acids per dry cell (1 mg), FIG. 3C: Composition of each fatty acid (%) with respect to the total fatty acid amount. Host strain: control; G#18 and G#22: strains prepared in Example 3; C#14 and C#16: strains prepared in Example 5.

DESCRIPTION OF EMBODIMENTS

Figure 1:
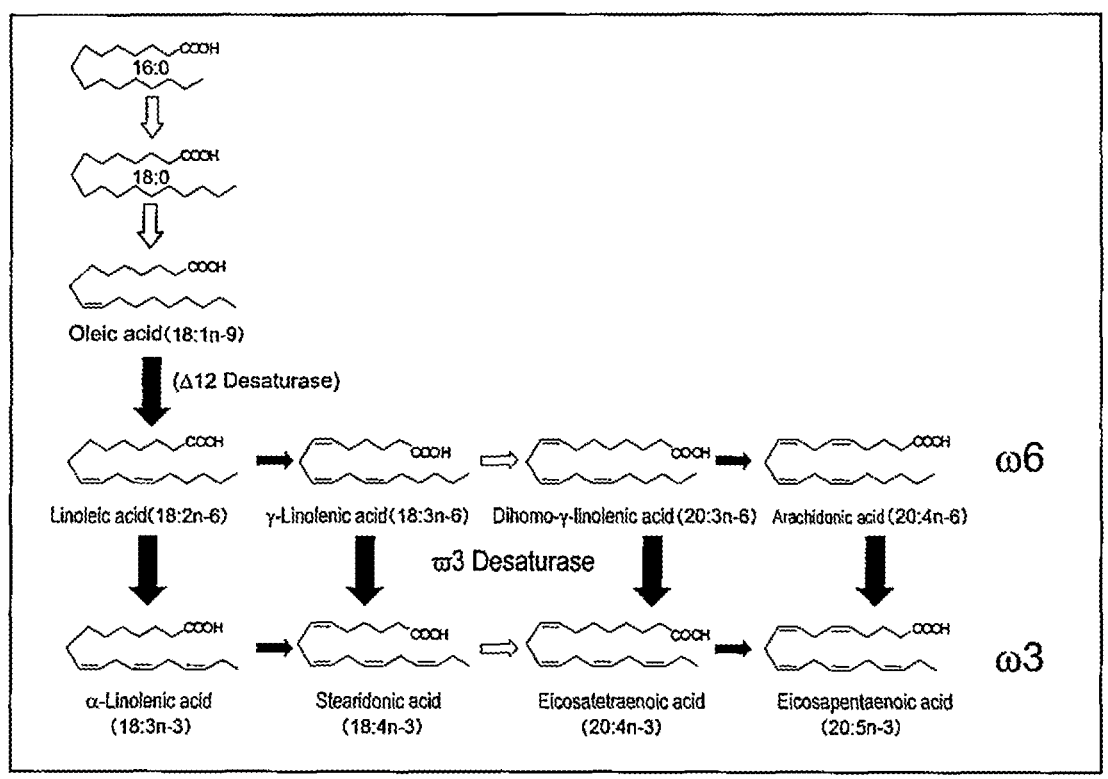
FIG. 1 shows fatty acid biosynthetic pathway in *Mortierella alpina* 1S-4.

In the specification, unless otherwise specified, "one or more" used in deletion, substitution, addition or insertion of an amino acid(s) or a nucleotide(s) in an amino acid sequence or a nucleotide sequence can refer to, for example, 1 to 20, preferably 1 to 10, more preferably 1 to 5, further preferably 1 to 4, still further preferably 1 to 3 and further more preferably 1 or 2. In the specification, the "addition" of an amino acid(s) or a nucleotide(s) includes addition of one or more amino acids or nucleotides to one end and both ends of a sequence.

In the specification, the identity of amino acid sequences or nucleotide sequences can be determined based on algorithm BLAST (Pro. Natl. Acad. Sci. USA, 1993, 90: 5873-5877) by Karlin and Altschul or FASTA (Methods Enzymol., 1990, 183: 63-98). Based on the algorithm BLAST, programs called as BLASTN and BLASTX have been developed (J. Mol. Biol., 1990, 215: 403-410). When a nucleotide sequence is analyzed by BLASTN based on BLAST, parameters, for example, Score=100 and wordlength=12, are used. Furthermore, when an amino acid sequence is analyzed by BLASTX based on BLAST, parameters, for example, score=50 and wordlength=3, are used. When BLAST and Gapped BLAST program are used, default parameters of each program are used. Specific manners of these analysis methods are known (see, www.ncbi.nlm.nih.gov).

In the specification, "stringent conditions" refer to the conditions where nucleotide sequences having a high identity, for example, 90% or more, 95% or more, 98% or more, or 99% or more are mutually hybridized; however, nucleotide sequences having a lower identity are not mutually hybridized. More specifically, the "stringent conditions" in the specification can be appropriately changed depending upon the degree of a desired identity. As the conditions become more stringent, only a sequence having a higher identity comes to be hybridized. Examples of less stringent conditions include a washing condition of 5×SSC, 5×Denhardt's solution, 0.5% SDS, 50% formamide at about 32 to 50° C. Examples of highly stringent conditions include a washing condition of 6×SSC, 0.01M EDTA, 1×Denhardt's solution, 0.5% SDS at about 55 to 68° C.; or a washing condition of 5×SSC, 5×Denhardt's solution, 0.5% SDS, 50% formamide at about 55° C. to 68° C. As other factors having an effect on hybridization, a plurality of factors such as concentration and length of a probe and reaction time may be considered. Those skilled in the art can determine appropriate stringency by appropriately selecting the conditions and factors as mentioned above with reference to, for example, Sambrook et al., Molecular Cloning, A Laboratory Manual, 3rd Ed., Cold Spring Harbor Laboratory (2001).

In the specification, "corresponding position" or "corresponding region" of a target amino acid sequence or a nucleotide sequence to a specific position or region on a specific amino acid sequence or nucleotide sequence can be determined by aligning, the target amino acid sequence or nucleotide sequence with the specific sequence serving as a reference (reference sequence) such that conservative amino acid residues or nucleotides present in individual amino acid sequences or nucleotide sequences have a maximum homology. Alignment can be carried out by use of a known algorithm and its procedure is known to those skilled in the art. For example, alignment, although it can be manually performed based on the Lipman-Pearson method as described above, can be performed by using the Clustal W multiple alignment program (Thompson, J. D. et al., 1994, Nucleic Acids Res., 22: 4673-4680) by default. Alternatively, a revised edition of Clustal W, e.g., Clustal W2 and Clustal omega, can be used. Clustal W, Clustal W2 and Clustal omega are available, for example, on the web sites of the European Bioinformatics Institute: (EBI [www ebi. ac.uk/index .html]) and the DNA Data Bank of Japan (DDBJ [www ddbj.nig.ac.jp/Welcome-j .html]) run by the National Institute of Genetics.

In the specification, the "ω6 highly unsaturated fatty acid metabolic pathway" refers to a metabolic pathway for producing an ω6 highly-unsaturated fatty acid such as γ-linolenic acid (GLA, 18: 3n−6), dihomo-γ-linolenic acid (DGLA, 20: 3n−6) and arachidonic acid (ARA, 20: 4n−6) from linoleic acid (LA, 18: 2n−6); and the "ω3 highly unsaturated fatty acid metabolic pathway" refers to a metabolic pathway for producing an ω3 highly-unsaturated fatty acid such as stearidonic acid (SDA, 18: 4n−3), eicosatetraenoic acid (ETA, 20: 4n−3) and eicosapentaenoic acid (EPA, 20: 5n-3) from α-linolenic acid (ALA, 18: 3n-3) (see, FIG. 1). In the specification, the "highly-unsaturated fatty acid" refers to a long-chain fatty acid having 18 or more carbon atoms and 2 or more unsaturated bonds. Further, in the specification, "C20 ω̄3 unsaturated fatty acid" refers to ω̄3 highly-unsaturated fatty acid having 20 carbon atoms, such as EPA and ETA.

In the specification, the "desaturation activity" refers to an activity to introduce a carbon-carbon double bond into a fatty acid chain; and the "desaturase" refers to a protein or polypeptide having the desaturation activity. The desaturation activity and desaturase are subdivided based on the position on a fatty acid to which a carbon-carbon double bond is introduced by the activity. For example, the "ω̄3 desaturation activity" refers to an activity to introduce a double bond between the third and fourth carbon from the ω̄ end of a fatty acid and the "ω̄3 desaturase" refers to an enzyme having the ω̄3 desaturation activity and producing an ω̄3 unsaturated fatty acid. Examples of the ω̄3 desaturase may include a conversion enzyme from LA (18: 2n-6) to ALA (18: 3n-3), a conversion enzyme from GLA (18: 3n-6) to SDA (18: 4n-3), a conversion enzyme from DGLA (20: 3n-6) to ETA (20: 4n-3) and a conversion enzyme from ARA (20: 4n-6) to EPA (20: 5n-3).

In the specification, the "Δ17 desaturation activity" refers to an activity to introduce a double bond between 17th and 18th carbon atoms from the carboxyl end of a fatty acid; and the "Δ17 desaturase" is an enzyme having the above activity and producing a Δ17 unsaturated fatty acid. For example, the Δ17 desaturase may include a conversion enzyme from DGLA (20: 3n-6) into ETA (20: 4n-3) and a conversion enzyme from ARA (20: 4n-6) into EPA (20: 5n-3).

"ω̄3 Desaturase" and "Δ17 desaturase" serve to introduce an unsaturated bond into the same position (between the third and fourth carbon atoms from the ω̄ end=between 17th and 18th carbon atoms from the carboxyl end) of a C20 fatty acid. Accordingly, in the specification, the "ω̄3 desaturation activity on a C20 fatty acid" can be rephrased as the "Δ17 desaturation activity".

In the specification, "having enzymatic activity at normal temperature" means that the optimum temperature of the enzymatic activity is 20° C. or more and preferably 20 to 40° C. or that the enzymatic activity at 20° C. corresponding to 70% or more and preferably 80% or more of the enzymatic activity at the optimum temperature. For example, in the specification, an enzyme having "the ω̄3 desaturation activity on a C20 fatty acid at normal temperature" means that the optimum temperature of the ω̄3 desaturation activity of the enzyme on a C20 fatty acid is 20 to 40° C., or that the ω̄3 desaturation activity of the enzyme on a C20 fatty acid at 20° C. is 70% or more and preferably 80% or more of the ω̄3 desaturation activity of the enzyme on a C20 fatty acid at the optimum temperature.

In the specification, the term "inherent" used in mentioning function, properties and trait of a microorganism is used to express that the function, properties and trait are those present in a wild type of microorganism. In contrast, the term "exogenous" is used to express that the function, properties and trait are not originally present in the microorganism but externally introduced. For example, a gene externally introduced into a microorganism is an exogenous gene. The exogenous gene may be a gene derived from the same species as the microorganism to which the exogenous gene is to be introduced or may be a gene derived from a heterologous organism.

The ω̄3 desaturase provided by the present invention is a polypeptide which consists of an amino acid sequence having an identity of 80% or more with the amino acid sequence represented by SEQ ID NO: 2 and has ω̄3 desaturation activity on a C20 fatty acid at normal temperature. As an example of the polypeptide, a polypeptide consisting of the following amino acid sequence and having ω̄3 desaturation activity on a C20 fatty acid at normal temperature is mentioned.

(A) the amino acid sequence represented by SEQ ID NO: 2;

(B) an amino acid sequence having an identity of 90% or more, preferably 95% or more, more preferably 98% or more, and further preferably 99% or more with the amino acid sequence represented by SEQ ID NO: 2;

(C) an amino acid sequence obtained by subjecting the amino acid sequence represented by SEQ ID NO: 2 to mutation selected from the group consisting of deletion, substitution, insertion and addition of one or more amino acids.

(D) an amino acid sequence represented by SEQ ID NO: 4;

(E) an amino acid sequence having an identity of 90% or more, preferably 95% or more, more preferably 98% or more, and further preferably 99% or more with the amino acid sequence represented by SEQ ID NO: 4;

(F) an amino acid sequence obtained by subjecting the amino acid sequence represented by SEQ ID NO: 4 to mutation selected from the group consisting of deletion, substitution, insertion and addition of one or more amino acids.

In the amino acid sequence above, the position at which an amino acid(s) is(are) deleted, substituted, inserted and added is not particularly limited as long as the mutated polypeptide maintains the ω̄3 desaturation activity on a C20 fatty acid at normal temperature.

As the ω̄3 desaturase of the present invention, proteins having the aforementioned amino acid sequences (A) to (F), in which individual amino acids may be substituted with amino acids belonging to a group of amino acids analogous in feature, are mentioned. The position and number of amino acids to be substituted with analogous amino acids are not particularly limited as long as the polypeptide obtained after substitution maintains the ω̄3 desaturation activity on a C20 fatty acid at normal temperature. Examples of the amino acids analogous in feature include glycine and alanine; valine, leucine and isoleucine; serine and threonine; aspartic acid and glutamic acid; asparagine and glutamine; lysine and arginine; cysteine and methionine; and phenylalanine and tyrosine.

The ω̄3 desaturase of the present invention is preferably an ω̄3 desaturase which specifically acts on a C20 fatty acid at normal temperature, preferably at a temperature of 20° C. to 40° C.

Both of the ω̄3 desaturases represented by SEQ ID NO: 2 and SEQ ID NO: 4 are enzymes derived from a *Mastigomycotina* (*Plectospira myriandra*). As a result of BLAST analysis, it was found that the ω̄3 desaturases represented by SEQ ID NO: 2 and SEQ ID NO: 4 are novel polypeptides having a high amino acid sequence identity of about 98.9% to each other; whereas, the amino acid sequences are extremely different from those of proteins known in the art. The sequence identity of the amino acid sequence of the ω̄3 desaturases represented by SEQ ID NO: 2 and SEQ ID NO: 4 with the amino acid sequence of ω̄3 desaturase known in the art derived from e.g., *Saprolegnia* (for example, ω̄3 desaturases disclosed in Patent Literatures 4 to 6) is at most 70%.

The present inventors constructed a polynucleotide consisting of a suspected ORF encoding the ω3 desaturase based on the genome of *Plectospira myriandra*. The polynucleotide is a polynucleotide consisting of the nucleotide sequence represented by SEQ ID NO: 1 and encoding the ω3 desaturase of the present invention represented by SEQ ID NO: 2. The present inventors obtained cDNA consisting of the nucleotide sequence represented by SEQ ID NO: 3 by a reverse transcription reaction to a target, *Plectospira myriandra* mRNA. This is a polynucleotide encoding the ω3 desaturase of the present invention represented by SEQ ID NO: 4. Accordingly, both of the polynucleotides consisting of the nucleotide sequences represented by SEQ ID NO: 1 and SEQ ID NO: 3 are polynucleotides containing no intron sequence and different from the genomic DNA present in a *Plectospira myriandra* cell.

Accordingly, the present invention further provides a polynucleotide encoding the ω3 desaturase of the present invention (hereinafter referred to also as the ω3 desaturase gene of the present invention). As an example of the ω3 desaturase gene of the present invention, a polynucleotide encoding a polypeptide consisting of the following nucleotide sequence and having ω3 desaturation activity on a C20 fatty acid at normal temperature or a complementary strand thereof is mentioned.

(a) a nucleotide sequence represented by SEQ ID NO: 1;

(b) a nucleotide sequence having an identity of 90% or more, preferably 95% or more, more preferably 98% or more, and further preferably 99% or more with the nucleotide sequence represented by SEQ ID NO: 1, (c) a nucleotide sequence obtained by subjecting the nucleotide sequence represented by SEQ ID NO: 1 to mutation selected from the group consisting of deletion, substitution, insertion and addition of one or more nucleotides;

(d) a nucleotide sequence hybridizing with the nucleotide sequence represented by SEQ ID NO: 1 in stringent conditions;

(e) a nucleotide sequence represented by SEQ ID NO: 3;

(f) a nucleotide sequence having an identity of 90% or more, preferably 95% or more, more preferably 98% or more, and further preferably 99% or more with the nucleotide sequence represented by SEQ ID NO: 3

(g) a nucleotide sequence obtained by subjecting the nucleotide sequence represented by SEQ ID NO: 3 to mutation selected from the group consisting of deletion, substitution, insertion and addition of one or more nucleotides; or, (h) a nucleotide sequence hybridizing with the nucleotide sequence represented by SEQ ID NO: 3 in stringent conditions.

The position at which a nucleotide(s) is(are) deleted, substituted, inserted and added is not particularly limited as long as the polypeptide encoded by the mutated polynucleotide maintains ω3 desaturation activity on a C20 fatty acid at normal temperature.

The ω3 desaturase of the present invention can be produced in accordance with a known method, preferably by chemical synthesis or biological synthesis. As an example of the chemical synthesis, a method of extending a peptide chain by sequentially connecting amino acids having a side-chain functional group(s) protected in accordance with an ordinary method may be mentioned. As an example of the biological synthesis, a method including expressing the ω3 desaturase of the present invention from the ω3 desaturase gene of the present invention, isolating the enzyme produced, and, if necessary, further purifying the enzyme, may be mentioned.

Now, the method for biologically synthesizing the ω3 desaturase of the present invention will be more specifically described below. First, the ω3 desaturase gene of the present invention is prepared. The gene may be produced in accordance with a chemical synthesis method known in the art based on the amino acid sequence of the ω3 desaturase of the present invention and sequence information of genomic DNA of a microorganism such as *Plectospira myriandra* or may be isolated from a microorganism such as *Plectospira myriandra* described above. When the ω3 desaturase gene of the present invention is isolated from a microorganism, for example, a cDNA library is prepared from total RNA of the microorganism and cDNA of a desired gene of the present invention can be isolated by screening the cDNA library. In screening, a probe or primer is designed based on the nucleotide sequence of the gene of the present invention and cDNA hybridizing with the probe or primer in stringent conditions may be selected. Alternatively, desired cDNA can be selectively synthesized from the total RNA of the microorganism by a sequence-specific reverse transcription reaction. The cDNA selected can be amplified by a known method such as PCR.

Alternatively, the ω3 desaturase gene of the present invention can be prepared by introducing mutation by a known mutagenesis method such as ultraviolet irradiation and site-specific mutagenesis into a gene isolated or synthesized in the aforementioned procedure. For example, mutation is introduced by a known method to a polynucleotide represented by SEQ ID NO: 1 or SEQ ID NO: 3 to obtain a mutated polynucleotide. The ω3 desaturase gene of the present invention can be obtained by determining the ω3 desaturation activity of a polypeptide expressed by the mutated polynucleotide and selecting a gene encoding a polypeptide having a desired activity.

The ω3 desaturase gene of the present invention prepared by the aforementioned procedure, codon optimization is preferably performed in accordance with the frequency of codon usage in a cell into which the gene is introduced and expressed. The information of codons used in various organisms is available in the Codon Usage Database (www kazusa.or .jp/codon/). For example, if codon optimization of ω3 desaturase genes represented by SEQ ID NO: 1 and SEQ ID NO: 3 is performed in accordance with the frequency of codon usage (www kazusa.or .jp/codon/cgi-bin/showcodon-.cgi?species=64518) of *Mortierella alpina* (*Mortierella alpina*), polynucleotides represented by SEQ ID NO: 5 and SEQ ID NO: 6 are resulted, respectively. Accordingly, as the ω3 desaturase gene of the present invention, a polynucleotide obtained by subjecting basically a polynucleotide consisting of any one of the nucleotide sequences described in (a) to (h) to codon optimization in accordance with the frequency of codon usage in each organism, is mentioned.

Next, the ω3 desaturase of the present invention is expressed from the ω3 desaturase gene of the present invention prepared. Although the enzyme may be expressed in an acellular system, the ω3 desaturase gene of the present invention is introduced into a host cell to obtain a transformed cell, and then, the ω3 desaturase of the present invention is allowed to express in the transformed cell.

As a host cell to which the ω3 desaturase gene of the present invention is to be introduced, microbial cells such as bacterial, fungal and algal cells are preferable but the host cell is not particularly limited to these. The ω3 desaturase gene of the present invention can be introduced into a host cell by use of a vector containing the gene. The type of vector to be used for introduction can be appropriately selected depending upon the type of host cell, cloning method, gene expression method and the like. For example, when the ω3 desaturase of the present invention is directly expressed from the gene on the vector present outside the genome of a cell, an expression vector is preferably used. The ω3 desaturase gene of the present invention is integrated into an appropriate vector. The resultant vector containing the ω3 desaturase gene of the present invention is introduced into a host cell. The vector can be introduced into a cell by use of a known method such as an electroporation method, a particle gun (gene gun) method, a competent cell method, a protoplast method, a calcium phosphate coprecipitation method, *Agrobacterium tumefaciens*-mediated transformation (ATMT) method and its modification method (Appl. Environ. Microbiol., 2009, 75: 5529-5535). At this time, if an appropriate marker gene is integrated into a vector, a transformed cell having the vector containing the gene of the present invention introduced therein can be screened out based on marker expression as an index.

The ω3 desaturase of the present invention is expressed by the transformed cell. The ω3 desaturase of the present invention expressed can be isolated or if necessary, purified by a known protein isolation or purification method.

The ω3 desaturase of the present invention has a high ω3 desaturation activity at normal temperature of, for example, 20° C. or more at which cells easily proliferate and can play a role in biological synthesis of a C20 ω3 unsaturated fatty acid such as EPA. Thus, a cell expressing the ω3 desaturase of the present invention is cultured at normal temperature, the cell can easily proliferate and a C20 ω3 unsaturated fatty acid is biologically synthesized by the ω3 desaturase of the present invention expressed in the proliferated cell, with the result that a C20 ω3 unsaturated fatty acid such as EPA can be efficiently produced.

Accordingly, the present invention provides a method for producing a C20 ω3 unsaturated fatty acid including culturing a cell expressing the ω3 desaturase of the present invention. As the C20 ω3 unsaturated fatty acid, ETA and EPA are mentioned and preferably EPA is mentioned. The present invention provides a method for producing an EPA-containing lipid, including culturing a cell expressing the ω3 desaturase of the present invention. The present invention further provides a method for producing EPA, including purifying the EPA-containing lipid produced by the EPA-containing lipid production method of the present invention.

The cell for expressing the ω3 desaturase of the present invention may be a cell inherently expressing the enzyme or a cell modified so as to express the enzyme. As the cell inherently expressing the ω3 desaturase of the present invention, *Plectospira myriandra* is mentioned. As the cell modified so as to express the ω3 desaturase of the present invention, the aforementioned transformed cell, which has acquired expressional potency of the ω3 desaturase of the present invention by introduction of the ω3 desaturase gene of the present invention, is mentioned. The transformed cell may be any cell derived from e.g., plants, bacteria, fungi and algae; however, microbial cell derived from e.g., bacteria, fungi and algae is preferable. Alternatively, a cell of *Plectospira myriandra* as mentioned above, which is modified so as to improve expression of the ω3 desaturase of the present invention, can be used as a method for producing an EPA-containing lipid of the present invention.

In the method for producing an EPA-containing lipid of the present invention, the cell expressing the ω3 desaturase of the present invention produces EPA by the action of the ω3 desaturase of the present invention. Thus, the cell not only has an expressional potency of the ω3 desaturase of the present invention but also inherently has an ability to produce arachidonic acid (ARA) serving as a substrate for the enzyme or is modified so as to produce ARA. Preferably, the cell inherently has an ω6 highly unsaturated fatty acid metabolic pathway or is modified so as to have the pathway. More preferably, the cell inherently has an ω6 highly unsaturated fatty acid metabolic pathway and an ω3 highly unsaturated fatty acid metabolic pathway or modified so as to have the both pathways. As shown in FIG. 1, ARA produced via the ω6 highly unsaturated fatty acid metabolic pathway is converted into EPA by the action of ω3 desaturase. Alternatively, a C20 ω6 highly-unsaturated fatty acid such as DGLA is converted into a C20 ω3 highly-unsaturated fatty acid such as ETA by the action of the ω3 desaturase and then EPA is produced from each of these ω3 highly-unsaturated fatty acids via the ω3 highly unsaturated fatty acid metabolic pathway.

As a preferable example of the cell to be used in the method for producing an EPA-containing lipid of the present invention, cells of oleaginous microorganisms having a potency of expressing the ω3 desaturase of the present invention and an ω6 highly unsaturated fatty acid metabolic pathway and capable of producing arachidonic acid are mentioned. More preferably, the oleaginous microorganism further has an ω3 highly unsaturated fatty acid metabolic pathway. Examples of such an oleaginous microorganism include *Plectospira myriandra*, as mentioned above; and an oleaginous microorganism having an ability to produce arachidonic acid via the ω6 highly unsaturated fatty acid metabolic pathway, preferably an oleaginous microorganism having an ω3 highly unsaturated fatty acid metabolic pathway and modified so as to express the ω3 desaturase of the present invention.

The oleaginous microorganism modified so as to express the ω3 desaturase of the present invention can be obtained by introducing the ω3 desaturase gene of the present invention into an oleaginous microorganism having an ω6 highly unsaturated fatty acid metabolic pathway and an ability to produce arachidonic acid, and preferably having an ω3 highly unsaturated fatty acid metabolic pathway. Introduction of the ω3 desaturase gene of the present invention into the oleaginous microorganism can be carried out in accordance with the aforementioned procedure for introducing a gene to a host cell. Specific procedure thereof will be described below.

Examples of the oleaginous microorganism to which the ω3 desaturase gene of the present invention is to be introduced include, but are not limited to, the genus *Plectospira*, yeast, and filamentous bacteria belonging to e.g., the genus *Mortierella*, the genus *Mucor* and the genus *Umbelopsis*. Examples of the yeast include ascomycetous yeast, basidiomycetous yeast, fission yeast and budding yeast. Among these, preferable examples include *Mortierella* microorganisms such as *Mortierella alpina* (hereinafter sometimes referred to as *M. alpina*), *Mortierella chlamydospora*, *Mortierella elongata*, *Mortierella exigua*, *Mortierella hygrophila*, *Mortierella epigama*, *Mortierella acrotona*, *Mortierella minutissima*, *Mortierella lignicola*, *Mortierella clonocystis*, *Mortierella nana*, *Mortierella humicola*, *Mortierella bainieri*, *Mortierella hyaline*, *Mortierella globalpina*, *Umbelopsis nana* and *Umbelopsis isabellina*; and more preferably, *M. alpina*, *Mortierella clonocystis*, *Mortierella nana*, *Mortierella humicola*, *Mortierella bainieri*, *Mortierella hyaline* and *Mortierella globalpina*.

The oleaginous microorganism to which the gene of the present invention is to be introduced may be a mutant strain of microorganism such as *Plectospira*, yeasts, *Mortierella*, *Mucor* and *Umbelopsis* as long as it has an ω6 highly unsaturated fatty acid metabolic pathway and has an ability to produce arachidonic acid. The mutant strain, since it needs not to express an ω3 desaturase except the ω3 desaturase of the present invention, may be a strain defective in ω3 desaturase which the microorganism inherently has. Examples of such a mutant strain and a defective strain include *M. alpina* 1S-4 (Agric. Biol. Chem., 1987, 51 (3): 785-790) and *M. alpina* ST1358 (Biosci. Biotechnol. Biochem., 2010, 74: 908-917).

The mutant strain and deficient strain of the oleaginous microorganism can be obtained by a conventional method, for example, a treatment with a mutagen such as ethyl methane sulfonate (EMS), methyl methane sulfonate (MMS), N-methyl-N-nitro-N-nitrosoguanidine (J. Gen. Microbiol., 1992, 138: 997-1002), 5-bromodeoxyuridine (BrdU), cisplatin and mitomycin C; and mutation induction by e.g., radiation irradiation, ultraviolet irradiation and heat treatment; or e.g., suppression of gene expression by RNAi.

The ω3 desaturase gene of the present invention may be introduced into the genome of the aforementioned microorganism or integrated into an expression vector and introduced in a cell outside the genome. In either case, the ω3 desaturase gene of the present invention is preferably introduced together with the vector having the gene integrated therein. The vector to be used for gene transfer can be appropriately selected by those skilled in the art depending upon the type of microorganism to which the gene is to be introduced, the cloning method and gene expression method and the like. Examples of the vector for use in introducing a gene into the *Mortierella* microorganism outside the genome thereof include pD4 vector (Appl. Environ. Microbial., 2000, 66 (11): 4655-4661), pDZeo vector (J. Biosci. Bioeng., 2005, 100 (6): 617-622), pDuraS vector (Appl. Microbial. Biotechnol., 2004, 65 (4): 419-425), pDX vector (Curr. Genet., 2009, (3): 349-356) and pBIG3ura5 (Appl. Environ. Microbiol., 2009, 75: 5529-5535).

It is preferable that the aforementioned vectors contain a promoter sequence or a transcription termination signal sequence for expressing the gene of the present invention integrated or a selective marker gene for selecting a transformant having a desired gene introduced therein. As the promoter, a hyper-expression promoter is preferable. Examples of a preferable hyper-expression promoter for a *Mortierella* microorganism include *M. alpina*-derived PP3 promoter and SSA2 promoter, and modified promoters thereof obtained by subjecting the sequences of these promoters a substitution, a deletion or an addition. The hyper-expression promoter is not limited to these as long as the gene introduced can be highly expressed. Examples of the selective marker gene include drug resistant genes such as a kanamycin resistant gene, a streptomycin resistant gene, a carboxin resistant gene, a Zeocin resistant gene and a hygromycin resistant gene; genes compensating an auxotrophic mutation of an amino acid such as leucine, histidine, methionine, arginine, tryptophan and lysine; and genes compensating an auxotrophic mutation of a nucleic acid base such as uracil and adenine. As an example of the preferable selective marker gene, a gene compensating an auxotrophic mutation of uracil is mentioned. For example, an uracil auxotrophic mutant strain of *M. alpina* (Biosci. Biotechnol. Biochem., 2004, 68: 277-285) is developed. To such an uracil auxotrophy strain, a selective marker gene such as an orotidine-5'-phosphate decarboxylase gene (ura3 gene) or an orotidylic acid pyrophosphorylase gene (ura5 gene) can be used. The procedure for constructing a vector and the types of reagents, e.g., a restriction enzyme or a ligation enzyme, are not particularly limited. Those skilled in the art can construct a vector in accordance with general technical knowledge or by appropriately using commercial products.

Figure 2:
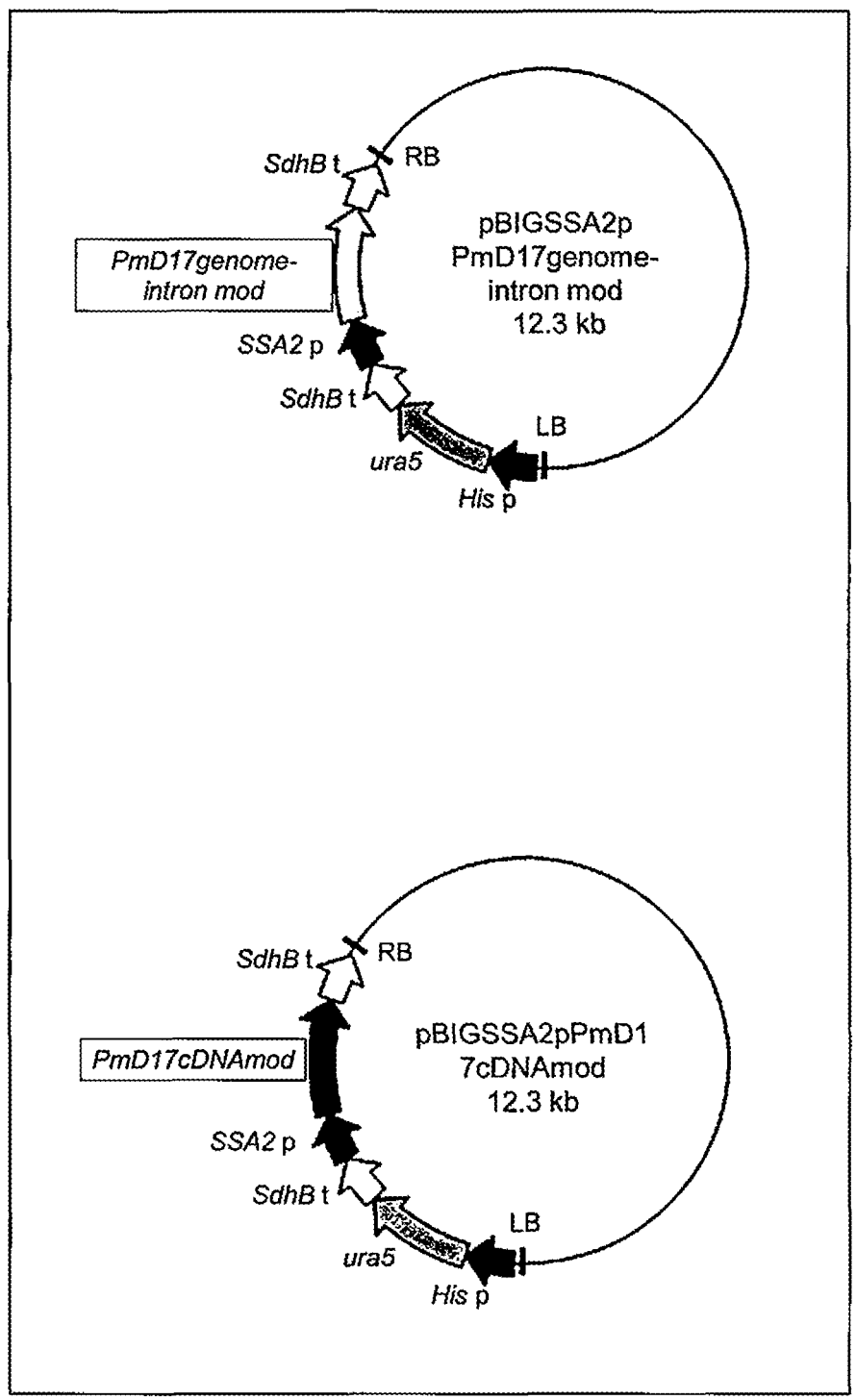
FIG. 2 shows a binary vector for transforming *Mortierella alpina*.

An example of the transformation binary vector, which can be used in introduction of the ω3 desaturase gene of the present invention into *M. alpina*, is shown in FIG. 2. In the vector, a polynucleotide encoding the ω3 desaturase of the present invention (PmD17XXmod) is ligated downstream of a constitutive hyper-expression promoter, i.e., SSA2 promoter, and further, a terminator such as sdhB terminator and a selective marker for a transformant, i.e., ura5 gene, are integrated.

As a method for directly introducing the ω3 desaturase gene of the present invention into the genome of a microorganism, homologous recombination is mentioned. The gene of the present invention and a vector having a complementary sequence of a target genome to be introduced are prepared and then the vector is introduced into the microorganism. In this manner, the ω3 desaturase gene of the present invention is integrated into the target position on the genome of the microorganism by homologous recombination. In the vector, if necessary, a promoter sequence, a transcription termination signal sequence or a selective marker gene as mentioned above may also be integrated.

A means for introducing a vector into a microorganism may be appropriately selected by those skilled in the art depending upon the type of microorganism and vector. For example, if the vector is introduced into a fungus such as a *Mortierella* microorganism, an electroporation method, a particle gun (gene gun) method, an ATMT method and its modified method (Appl. Environ. Microbiol., 2009, 75: 5529-5535) are mentioned and an ATMT method and its modification method are preferable. However, as long as a transformant stably maintaining a desired trait can be obtained, the gene transfer method is not limited to these methods.

The cell expressing the ω3 desaturase of the present invention to be used in the method for producing an EPA-containing lipid of the present invention may be modified such that the ω6 highly unsaturated fatty acid metabolic pathway is activated. For example, if a gene encoding Δ12 desaturase is introduced into the cell to highly express the enzyme, conversion from oleic acid to linoleic acid is accelerated in the cell to activate the ω6 highly unsaturated fatty acid metabolic pathway. If the pathway is activated, the amount of the ω6 highly unsaturated fatty acid serving as a substrate for the enzyme of the present invention is increased, with the result that production of EPA is accelerated. Alternatively, if a gene encoding Δ15 desaturase is introduced into the cell expressing the ω3 desaturase of the present invention to highly express the enzyme, a conversion from LA into ALA or GLA into SDA is accelerated to successfully activate the ω3 highly unsaturated fatty acid metabolic pathway. Further, to the cell expressing the ω3 desaturase of the present invention, the gene encoding Δ12 desaturase and the gene encoding Δ15 desaturase both may be introduced.

In the method for producing an EPA-containing lipid of the present invention, the cell expressing the ω3 desaturase of the present invention and obtained in the aforementioned procedure is inoculated in a liquid medium or in a solid medium and cultured. The conditions for culture can be optimized by those skilled in the art depending upon the type of cell. For example, if the cell is a fungus cell, spores or hyphae of the strain or a preculture solution obtained by previously culturing them can be inoculated on the aforementioned culture medium and cultured. Examples of the carbon source for the culture medium include, but are not limited to, glucose, fructose, xylose, saccharose, maltose, soluble starch, corn starch, glycerol, mannitol, a lipid, an alkane and an alkene. Examples of the nitrogen source include, but are not limited to, a natural nitrogen source such as peptone, yeast extract, malt extract, meat extract, casamino acid, corn steep liquor, soybean protein, defatted soybean, cotton seed meal and wheat bran; an organic nitrogen source such as urea; and an inorganic nitrogen source such as sodium nitrate, ammonium nitrate and ammonium sulfate. In addition, a lipid such as soybean oil, coconut oil and corn oil may be added. As the lipid to be added, a fat and oil rich in linoleic acid, such as soybean oil and corn oil, is preferable and soybean oil is more preferable. Moreover, as trace nutrients, mineral salts such as phosphate, magnesium sulfate, iron sulfate and copper sulfate or e.g., vitamin, can be appropriately added. These medium components are not particularly limited as long as they are used in concentrations which do not inhibit growth of the microorganism to be cultured. For example, the concentration of a carbon source in a culture medium is 0.1 to 40 mass %, and preferably 1 to 25 mass %; the concentration of a nitrogen source is 0.01 to 10 mass % and preferably 0.1 to 10 mass %. If *M. alpina* or its mutant strain is cultured, e.g., Czapek culture medium (described later), Czapek-dox culture medium, a glucose/yeast extract (hereinafter referred to as "GY") culture medium and SC culture medium can be suitably used. As to the culture medium for *Mortierella* microorganism, a known literature (e.g., International Publication WO No. 98/29558) may be used as a reference. The pH of the culture medium may be 4 to 10 and preferably 6 to 9. The culture may be carried out in accordance with aerated and agitated culture, shaking culture or static culture.

In order to increase the yield of EPA by accelerating the proliferation of the cell, the cell is preferably cultured at an optimum growth temperature. For example, the cell can be cultured at about 5 to 60° C., preferably about 10 to 50° C., more preferably about 10 to 40° C., further preferably about 20 to 40° C., and still further preferably about 20 to 30° C. For example, in the case of *M. alpina* or a mutant strain cell, culture may be performed at about 10 to 40° C., preferably about 20 to 40° C. and more preferably about 20 to 30° C. The culture period of the cell may be, for example 2 to 20 days and preferably 2 to 14 days. Note that as to a method for culturing a *Mortierella* microorganism, a known literature (e.g., JP-A6-153970) may be used as a reference.

By culturing a cell expressing the $\overline{\omega}3$ desaturase of the present invention in the above procedure, a lipid containing a large amount of EPA in the cell can be produced. After completion of the culture, the culture solution is treated by a conventional means such as centrifugation and filtration to separate cells. For example, the culture solution is centrifuged or filtered to remove liquid components. The separated cells are washed and then dried by e.g., lyophilization and air-drying, to obtain dry cells. From the cells, a desired lipid can be extracted by a known method such as extraction with an organic solvent. Examples of the organic solvent include a solvent highly dissolving a highly-unsaturated fatty acid and separable from water, such as hexane, ether, ethyl acetate, butyl acetate, chloroform, cyclohexane, benzene, toluene and xylene. These organic solvents can be used in combination. An organic solvent is distilled away from an extract at reduced pressure, etc., to extract a desired lipid. Alternatively, a lipid can be extracted from wet cells without drying cells. The obtained lipid may be further purified by an appropriate common method such as degumming, deacidification, deodorizing, decolorizing, column treatment and distillation.

In the above lipid extract, various types of fatty acids are contained as contaminants other than a target substance, EPA, of the method of the present invention. Thus, the lipid obtained above is further purified to successfully obtain EPA having a further higher purity. While EPA can be directly separated from the lipid, it is preferable that the fatty acids in the lipid are once converted into ester derivatives with a lower alcohol and then an ester derivative of a desired EPA is separated. Since the ester derivative can be separated by various separation and purification operations depending upon the carbon number, the number and position of double bonds and the like, a desired fatty acid ester derivative can be easily obtained. However, arachidonic acid, which has the same carbon number as EPA but differs by a single double bond, is difficult to separate from EPA. For the reason, the content of arachidonic acid in the lipid containing EPA is preferably low. The ester derivative is preferably an ethyl ester derivative. In esterification, a lower alcohol containing an acid catalyst such as hydrochloric acid, sulfuric acid and BF3 or a basic catalyst such as sodium methoxide and potassium hydroxide, can be used. From the obtained ester derivative, an ester derivative of desired EPA can be separated by using e.g., a silver complex method (for example, JP-B-2786748, JP-B-2895258, JP-B-2935555, JP-B-3001954), column chromatography, a low temperature crystallization method and a urea addition fractionation method, alone or in combination. The separated EPA ester derivative is hydrolyzed with an alkali, extracted with an organic solvent such as ether and ethyl acetate. In this manner, EPA can be purified. EPA may be purified in the form of a salt.

When the lipid containing a large amount of EPA according to the present invention is produced in an industrial scale, for example, an oleaginous microorganism expressing the $\overline{\omega}3$ desaturase of the present invention is cultured in a large scale in e.g., a tank, filtered by e.g., a filter press to collect cells, which are dried, fractured by e.g., a ball mill and extracted with an organic solvent to obtain the lipid. Other than this, there are many known methods of extracting a component in a microorganism in an industrial scale and purifying EPA from a lipid. These methods can be appropriately modified and used in the method of the present invention.

To produce ETA by using the $\overline{\omega}3$ desaturase of the present invention, the activity of $\Delta 5$ desaturase is preferably reduced in the cell expressing the $\overline{\omega}3$ desaturase of the present invention described above. In this manner, the cell produces mainly ETA in place of EPA. The reduction of $\Delta 5$ desaturase activity in the cell can be attained, for example, by expressing the enzyme of the present invention due to a $\Delta 5$ desaturase-deficient strain or inhibiting the expression of $\Delta 5$ desaturase in a cell due to RNAi. Culture of the cell, extraction of ETA-containing lipid from the cell and purification of ETA are carried out in the same procedure as in the case of EPA as mentioned above.

EPA, ETA or a salt thereof obtained in the present invention can be used for producing e.g., pharmaceuticals, cosmetics, food and feeds for human or nonhuman animals. Examples of dosage form of the pharmaceutical products include oral agents such as a tablet, a capsule, a granule, a powder, a syrup, a dry syrup, a solution and a suspension;

enteral formulations such as an enema agent and a suppository; drops; injections; external preparation; transdermal, mucosal, and nasal preparations; inhalation preparations; and patch. Examples of dosage form of the cosmetics include any form of cosmetics usually used, such as cream, milk, lotion, suspension, gel, powder, pack, sheet, patch, stick and cake.

Preferably, the pharmaceuticals or cosmetics may be a pharmaceutical or cosmetic for inhibiting platelet aggregation, lowering blood triglyceride, anti-arteriosclerosis, lowering blood viscosity, lowering blood pressure, anti-inflammation and antitumor. The pharmaceuticals or cosmetics contain EPA, ETA or a salt thereof as an active ingredient. The pharmaceuticals or cosmetics may further contain a pharmaceutically acceptable carrier or a cosmetically acceptable carrier. Examples thereof include an excipient, a disintegrant, a binder, a lubricant, a surfactant, a pH adjusting agent, a dispersing agent, an emulsifier, a preservative, an antioxidant, a coloring agent, an alcohol, water, a water-soluble polymer, a flavor, a sweetener, a flavoring agent and an acidulant. If necessary, other active ingredients such as medicinal ingredients and cosmetic ingredients may be contained. The pharmaceuticals or cosmetics can be produced by blending a carrier as mentioned above and other active ingredients with EPA, ETA or a salt thereof in accordance with the dosage form and preparing in accordance with a conventional method. The content of EPA or ETA in the above pharmaceuticals or cosmetics varies depending upon the dosage form and the content usually falls in the range of 0.1 to 99 mass % and preferably 1 to 80 mass %.

The above foods and drinks or feeds contain EPA, ETA or a salt thereof as an active ingredient. These foods and drinks or feeds may be health foods, functional foods and drinks, specified health foods and drink, foods and drinks for patients, feeds for e.g., livestock, racehorses and viewing animals and pet foods, which are expected to exert effects such as a platelet aggregation inhibitory effect, a blood triglyceride lowering action, an anti-arteriosclerosis effect, a blood viscosity-lowering effect, a blood pressure-lowering effect, an anti-inflammatory effect and anti-tumor effect, as described on labels.

The forms of the above foods and drinks or feeds are not particularly limited and all forms which allow to blend EPA, ETA or a salt thereof are included. The foods and drinks may be solid, semi-solid or liquid, in various forms such as a tablet, a chewable tablet, a powder, a capsule, a granule, a drink, a gel, a syrup and a liquid diet for tube enteral nutrition. Specific examples of the food and drink forms include tea drinks such as green tea, oolong tea and red tea; beverages such as a coffee drink, a soft drink, a jelly drink, a sports drink, a milk drink, a carbonated drink, a fruit juice drink, a lactic acid bacteria beverage, a fermented milk drink, a powdered beverage, a cocoa beverage, an alcoholic drink and purified water; spreads such as butter, jam and margarine; dried food sprinkled over rice, mayonnaise, shortening, custard cream, dressings, breads, cooked rice, noodles, pasta, miso soup, tofu, milk, yogurt, soup or sauces, and confectionery (e.g., biscuits and cookies, chocolate, candy, cake, ice cream, chewing gum, tablet). Since the feeds can employ almost the same compositions and forms as foods and drinks, the description as to foods and drinks in the specification can be applied to the feeds.

The foods and drinks or feeds as mentioned above can be produced by blending EPA, ETA or a salt thereof, other food and drink materials to be used for producing foods and drinks and feeds, nutrients, vitamins, minerals, amino acids, various oils and various additives (e.g., taste components, sweeteners, acidulants such as organic acids, surfactants, pH adjusting agents, stabilizers, antioxidants, dyes, flavors), and preparing according to conventional methods. Alternatively, the foods or drinks or feeds according to the present invention can be produced by blending EPA, ETA or a salt thereof to foods and drinks or feeds usually taken. The content of EPA or ETA in the foods and drinks or feeds varies depending upon the form thereof and the content usually falls in the range of 0.01 to 80 mass %, preferably 0.1 to 50 mass % and more preferably 1 to 30 mass %.

EXAMPLES

The present invention will be more specifically described by way of Examples; however, the technical range of the present invention is not limited to the following Examples.

(Culture Medium)

GY culture medium: 2% (w/v) glucose, 1% yeast extract.

Czapek-Dox agar medium: 3% sucrose, 0.2% $NaNO_3$, 0.1% $kH_2PO_4$, 0.05% KCL, 0.05% $MgSO_4.7H_2O$, 0.001% $FeSO_4.7H_2O$, 2% agar, pH6.0.

YPD medium: 20 g of polypeptone, 10 g of yeast extract, 0.4 g of adenine, 20 g of agar and 20 g of glucose dissolved in 1000 mL of water.

LB-Mg agar medium: 1% tryptone, 0.5% yeast extract, 85 mM NaCl, 0.5 mM $MgSO_4.7H_2O$, 0.5 mM NaOH, 1.5% agar, pH7.0.

Minimal medium (MM): 10 mM $K_2HPO_4$, 10 mM $KH_2PO_4$, 2.5 mM NaCl, 2 mM $MgSO4.7H_2O$, 0.7 mM $CaCl_2$, 9 μM $FeSO_4.7H_2O$, 4 mM $(NH_4)_2SO_4$, 10 mM glucose, pH7.0.

Induction medium (IM): To MM, 0.50 (w/v) glycerol, 200 μM acetosyringone and 40 mM 2-(N-morpholino)ethane sulfonic acid (MES) were added and pH was adjusted to 5.3.

SC culture medium: 5.0 g of Yeast Nitrogen Base w/o Amino Acids and Ammonium Sulfate (Difco), 1.7 g of $(NH_4)_2SO_4$, 20 g of glucose, 20 g of agar, 20 mg of adenine, 30 mg of tyrosine, 1.0 mg of methionine, 2.0 mg of arginine, 2.0 mg of histidine, 4.0 mg of lysine, 4.0 mg of tryptophan, 5.0 mg of threonine, 6.0 mg of isoleucine, 6.0 mg of leucine, 6.0 mg of L-phenylalanine.

Example 1 Identification of ω3 Desaturase

*Plectospira myriandra* was cultured in GY culture medium (10 mL) at 28° C. for 5 days while shaking, and cells were collected. The cells collected were placed in a 2-mL tube and fractured by use of a beads shocker (Yasui Kikai) at 1700 rpm for 10 seconds. This procedure was repeated twice. From fractured cells, mRNA was extracted by use of ISOGEN (Bio-Rad) in accordance with the manufacturer's protocol. The mRNA extracted was subjected to reverse transcription using Prime Script™ II High Fidelity RT-PCR Kit (TaKaRa) and primers: [5'-GAAATGGC-CGACGTGAACACCTCCTCGC-3' (SEQ ID NO: 7), and 5'-CTATGCGCGCTTGGTGAGCACCTCGC-3' (SEQ ID NO: 8)] to prepare cDNA represented by SEQ ID NO: 3. It was found that the cDNA encodes a polypeptide having the amino acid sequence represented by SEQ ID NO: 4.

Then, genomic DNA of *Plectospira myriandra* was screened from the sequence represented by SEQ ID NO: 3 and the corresponding genomic DNA sequence was identified. Further, a polynucleotide was designed based on the genomic DNA sequence by removing an intron(s). Based on the polynucleotide, DNA was chemically synthesized. The designed polynucleotide consisted of the nucleotide sequence represented by SEQ ID NO: 1 and encoded the polypeptide having the amino acid sequence represented by SEQ ID NO: 2. SEQ ID NO: 2 and SEQ ID NO: 4 differed in 4 amino acids of the whole amino acid sequence consisting of 355 residues (amino acid sequence identity was about 98.9%).

The cDNA (SEQ ID NO: 3) prepared in the above was integrated into a yeast expression vector, pYE22m (Biosci. Biotech. Biochem., 1995, 59: 1221-1228). The vector was introduced into *Saccharomyces cerevisiae* InvSc1 strain (tryptophan auxotrophy oleaginous yeast) by an electroporation method to obtain a transformant. Using the synthetic DNA (SEQ ID NO: 1) prepared above, a vector was constructed in the same manner as above and a transformed strain was prepared. Each of the transformed strains was cultured in YPD medium at 28° C. for a day and a polypeptide was expressed by the cDNA integrated. Note that $\overline{\omega}3$ desaturase inherent in the oleaginous yeast is not expressed in this culture condition. Subsequently, to the culture medium, an $\overline{\omega}6$ unsaturated fatty acid: linoleic acid (LA, 18: 2n-6), γ-linolenic acid (GLA, 18: 3n-6), dihomo-γ-linolenic acid (DGLA, 20: 3n-6), or arachidonic acid (ARA, 20: 4n-6) was added and cultured at 28° C. for two days. Thereafter the amounts of the corresponding $\overline{\omega}3$ unsaturated fatty acid: α-linolenic acid (ALA, 18: 3n-3), stearidonic acid (SDA, 18: 4n-3), eicosatetraenoic acid (ETA, 20: 4n-3) or eicosapentaenoic acid (EPA, 20: 5n-3) produced by $\overline{\omega}3$unsaturation were measured by gas-liquid chromatography (GLC).

As a result, C20 DGLA and ARA were each converted into the corresponding $\overline{\omega}3$ unsaturated fatty acids; whereas, C18 LA and GLA were not converted into the corresponding $\overline{\omega}3$ unsaturated fatty acids. From this, it was verified that the polypeptide (SEQ ID NO: 2) encoded by the synthetic DNA (SEQ ID NO: 1) and the polypeptide (SEQ ID NO: 4) encoded by the cDNA (SEQ ID NO: 3) both are $\overline{\omega}3$ desaturase (more specifically, Δ17 desaturase) acting on C20 fatty acid in a substrate-specific manner at normal temperature (Table 1).

TABLE 1

| Number of carbon atoms | Substrate | Product | Conversion rate (%)*[1] | |
|---|---|---|---|---|
| | | | Synthetic DNA product (SEQ ID NO: 2) | cDNA product (SEQ ID NO: 4) |
| 18 | LA | ALA | 0 | 0 |
| 18 | GLA | SDA | 0 | 0 |
| 20 | DGLA | ETA | 22.99 | 32.64 |
| 20 | ARA | EPA | 33.05 | 47.69 |

*[1]Conversion rate (%) = [product amount/(substrate amount after reaction + product amount)] × 100

Example 2 Preparation of $\overline{\omega}3$ Desaturase Gene Introduction Vector The codon optimization of the nucleotide sequence represented by SEQ ID NO: 1 was performed in accordance with *M. alpina* to obtain the polynucleotide represented by SEQ ID NO: 5. Upstream and downstream of CDS of the polynucleotide represented by SEQ ID NO: 5, SpeI and BamHI sites were constructed and the resultant construct was cloned into a SpMA-RQ (ampR) plasmid. The plasmid prepared was treated with SpeI and BamHI restriction enzymes. The resultant fragment of the gene was ligated to pBIG35 plasmid (pBIG2RHPH2 plasmid provided from Kyoto Prefectural University was modified, described in Appl. Environ. Microbiol., 2009, 75: 5529-5535) containing a constitutive hyper expression promoter, SSA2 promoter, to construct an expression cassette. The expression cassette was further tandemly ligated to an uracil auxotrophy marker gene (ura 5) to construct a binary transformation vector, pBIGSSA2pPmD17genome-intron mod (FIG. 2).

Example 3 Preparation of $\overline{\omega}3$ Desaturase Gene-Introduced Strain

*M. alpina* (uracil auxotrophy strain) was cultured in a 0.05 mg/mL uracil-containing Czapek-Dox agar medium. A culture was recovered and then filtered by Miracloth (Calbiochem) to prepare a spore suspension of *M. alpina*. To the *M. alpina* (uracil auxotrophy strain), the pBIGSSA2pPmD17genome-intron mod vector constructed in Example 2 was introduced in accordance with the ATMT method (Appl. Environ. Microbiol., 2009, 75: 5529-5535) described below to prepare an $\overline{\omega}3$ desaturase introduced strain.

The above binary vector pBIGSSA2pPmD17genome-intron mod was introduced by electroporation into *Agrobacterium* cells (*Agrobacterium tumefaciens* C58C1, provided by Kyoto Prefectural University) and the *Agrobacterium* cells were cultured in LB-Mg agar medium at 28° C. for 48 hours. The vector-containing *Agrobacterium* cells were screened by a PCR method. The vector-containing *Agrobacterium* cells were cultured in minimum medium (MM) for 2 days and centrifuged at 5,800×g. A fresh induction medium (IM) was added to prepare a suspension. The suspension was subjected to induction culture performed by a rotary shaker for 8 to 12 hours, at 28° C. until $OD_{660}$ reached 3.7 from 0.4. After completion of the culture, the bacterial suspension (100 μL) was mixed with the same amount of *M. alpina* suspension ($10^8$ $mL^{-1}$) obtained above, applied to a co-culturing medium (the same composition as in IM except that 5 mM glucose was contained in place of 10 mM glucose, and 1.5% agar was contained) on which nitrocellulose membrane (diameter 70 mm; hardened low-ash grade 50, Whatman) was placed, and cultured at 23° C. for 2 to 5 days. After completion of the co-culturing, the membrane was transferred to uracil-free SC culture medium containing 50 g/mL cefotaxime, 50 g/mL spectinomycin and 0.03% Nile blue A (Sigma), and cultured at 28° C. for 5 days. Visible fungal filaments from fungus colonies were transferred to fresh uracil-free SC culture medium. The cell, which can grow in the uracil-free SC culture medium and cannot grow in GY culture medium containing 5-fluoroorotic acid (5-FOA), was determined as $\overline{\omega}3$ desaturase gene-introduced strain stably maintaining the trait. To select a transformant stably maintaining the trait, the operation was repeated three times.

Example 4 Preparation of $\overline{\omega}3$ Desaturase Gene Introduction Vector The codon optimization of the nucleotide sequence represented by SEQ ID NO: 3 was performed in accordance with *M. alpina* to obtain the polynucleotide represented by SEQ ID NO: 6. A binary transformation vector, pBIGSSA2pPmD17cDNAmod, was constructed in the same manner as in Example 2 except that the polynucleotide represented by SEES ID NO: 6 was used (FIG. 2).

Example 5 Preparation of ω3 Desaturase Gene-Introduced Strain

An ω3 desaturase introduced strain was prepared in the same procedure as in Example 3 except that pBIGSSA2pPmD17cDNAmod was used as the gene transfer vector.

Example 6 Production of ω3 Unsaturated Fatty Acid by ω3 Desaturase Gene-Introduced Strain The ω3 desaturase gene introduced *M. alpina* strains obtained in Examples 3 and 5 were each aerobically cultured in a 4 mL of GY culture medium at 28° C. for 3, 7 and 10 days at 120 rpm. As the control, *M. alpina* strain having no ω3 desaturase gene introduced therein was cultured in the same manner. From each of the culture solutions, cells were collected by suction filtration and dried at 120° C. for 3 hours. To the dried cells, a dichloromethane solution (1 mL) containing a 0.5 mg/mL internal standard (containing saturated fatty acid having 23 carbon atoms which cannot be biosynthesized by *M. alpina*) and a hydrogen chloride methanol solution (2 mL) were added to methyl-esterify the fatty acid in a warm bath at 55° C. for 2 hours. To the reaction solution, distilled water (1 mL) and hexane (4 mL) were added and a hexane layer was extracted. The extract was centrifuged under reduced pressure to recover a fatty acid methyl ester.

The collected sample was dissolved in chloroform and subjected to gas-liquid chromatography (GLC) to determine the fatty acid composition in the sample. GLC was performed by use of GC-2010 (manufactured by Shimadzu Corporation) and capillary column TC70 (0.25 mm×60 m), manufactured by GL Sciences in the conditions: column temperature: 180° C., vaporizing-chamber temperature: 250° C., detector temperature: 250° C., carrier gas: He, make-up gas: $N_2$, a $H_2$ flow rate: 40 mL/min, air flow-rate: 400 mL/min, split ratio: 50, analysis time: 30 min. The amount of each fatty acid extracted was determined from a peak area value in the GLC chart based on the fatty acid amount of the internal standard and the amounts of each fatty acid per culture solution (1 mL) and per dry cell (1 mg) were calculated. In addition, the ratio of each fatty acid to the total fatty acid amount was obtained.

Figure 3A:
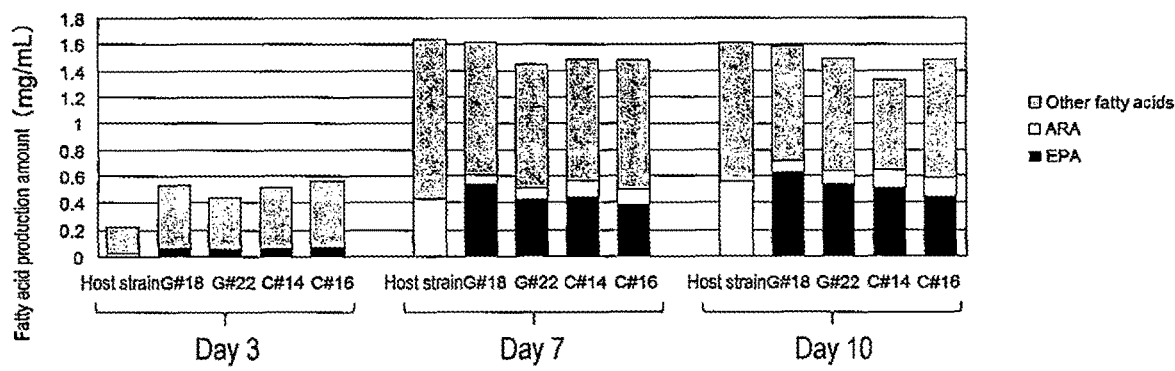
FIGS. 3A, 3B and 3C show production amounts of fatty acids of ω3 desaturase gene-introduced *Mortierella alpina* strains prepared in Examples 3 and 5.
Figure 3B:
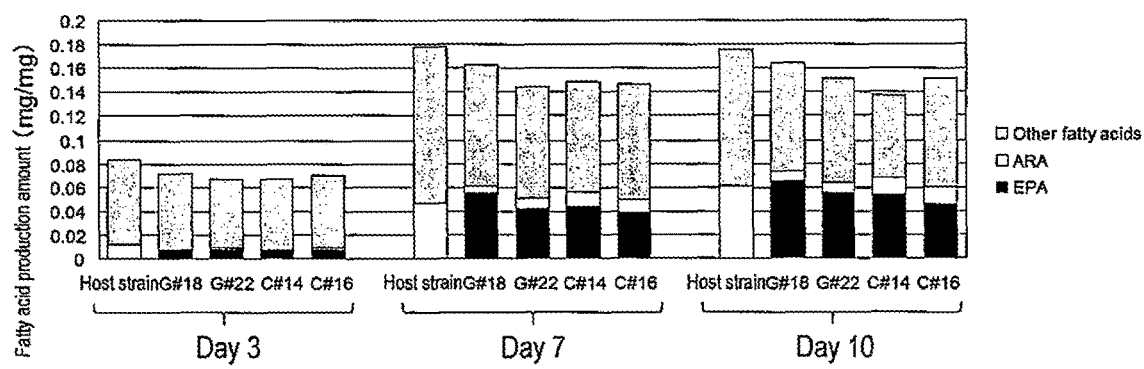
Figure 3C:
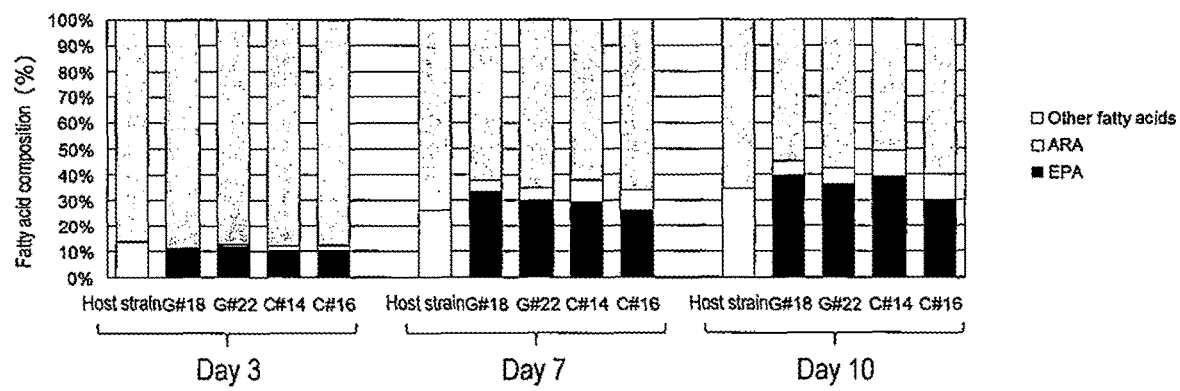

As a result, in the ω3 desaturase gene-introduced strains of Example 3 and Example 5, EPA accumulation were at most 40.8% and 39.6%, respectively (FIG. 3). In contrast, in the control strain, EPA was not produced (accumulation was not determined).

Example 7 Comparison of ω3 Desaturase Activity

The ω3 desaturation activity on a C20 fatty acid was compared between *Plectospira myriandra* having the ω3 desaturase of the present invention and *Saprolegnia diclina* (for example, Patent Literature 4) reported to have Δ17 desaturase. Further, other 8 closely related *Saprolegnia diclina* strains were checked for the ω3 desaturation activity.

*Plectospira myriandra* (NBRC No. 32548), *Saprolegnia diclina* (NBRC No. 32710) and other 8 strains listed in Table 2 were each cultured in 5 mL of GY culture medium at 28° C. for 7 days. After completion of the culture, the amounts of EPA (20: 5n–3) as the product of ω3 desaturase and ARA (20: 4n–6) as the substrate thereof in the medium were measured by gas-liquid chromatography (GLC).

As a result, as shown in Table 2, the content ratio of EPA to ARA in *Plectospira myriandra* was high compared to those of *Saprolegnia diclina* and the closely related strains. From the results, it was suggested that ω3 desaturase of *Plectospira myriandra* has a high conversion efficiency from ARA to EPA and is an enzyme which can efficiently produce EPA.

TABLE 2

| Strain | NBRC No. | EPA/ARA |
|---|---|---|
| *Plectospira myriandra* | 32548 | 0.66 |
| *Saprolegnia diclina* | 32710 | 0.53 |
| *Saprolegnia subterranean* | 104176 | 0.51 |
| *Aphanomyces iridis* | 31935 | 0.39 |
| *Salisapilia tartarea* | 32606 | 0.35 |
| *Achlya diffusa* | 102547 | 0.33 |
| *Dictyuchus sterilis* | 104178 | 0.21 |
| *Thraustotheca clavata* | 102130 | 0.14 |
| *Brevilegnia variabilis* | 104173 | 0.10 |
| *Halophytophthora epistomium* | 32618 | 0 |

The invention claimed is:

1. A polypeptide, consisting of an amino acid sequence of SEQ ID NO: 2, except that at least 5 and no more than 20 amino acids of the polypeptide are modified relative to the amino acid sequence of SEQ ID NO: 2 by mutations selected from the group consisting of a deletion, a substitution, an insertion and an addition,
wherein said polypeptide has ω3 desaturation activity on a C20 fatty acid.

2. A polypeptide, consisting of an amino acid sequence of SEQ ID NO: 4, except that at least 5 and no more than 20 amino acids of the polypeptide are modified relative to the amino acid sequence of SEQ ID NO: 4 by mutations selected from the group consisting of a deletion, a substitution, an insertion and an addition,
wherein said polypeptide has ω3 desaturation activity on a C20 fatty acid.

3. A cDNA polynucleotide encoding the polypeptide according to claim 1.

4. A cDNA polynucleotide, consisting of the following nucleotide sequence:
(a) the nucleotide sequence of SEQ ID NO: 1;
(b) a nucleotide sequence having an identity of 95% or more with the nucleotide sequence of SEQ ID NO: 1;
(c) a nucleotide sequence consisting of SEQ ID NO: 1, except that at least 1 and no more than 20 nucleotides of the nucleotide sequence are modified relative to SEQ ID NO: 1 by mutation selected from the group consisting of a deletion, a substitution, an insertion and an addition;
(d) the nucleotide sequence of SEQ ID NO: 3;
(e) a nucleotide sequence having an identity of 95% or more with the nucleotide sequence of SEQ ID NO: 3;
(f) a nucleotide sequence consisting of SEQ ID NO: 3, except that at least 1 and no more than 20 nucleotides of the nucleotide sequence are modified relative to SEQ ID NO: 3 by mutation selected from the group consisting of a deletion, a substitution, an insertion and an addition; or
(g) a nucleotide sequence obtained by optimizing a codon of any one of the nucleotide sequences of (a) to (f);
wherein the cDNA polynucleotide encodes a polypeptide having ω3 desaturation activity on a C20 fatty acid.

5. A vector, comprising the cDNA polynucleotide according to claim 4.

6. A microbial cell, comprising the cDNA polynucleotide according to claim 4.

7. A method for producing an eicosapentaenoic acid, the method comprising:
culturing the microbial cell according to claim 6, to obtain an eicosapentaenoic acid-containing lipid, and
purifying the eicosapentaenoic acid-containing lipid, to obtain an eicosapentaenoic acid.

8. The cDNA polynucleotide according to claim 4, consisting of the following nucleotide sequence:
(a) a nucleotide sequence having an identity of 98% or more with the nucleotide sequence of SEQ ID NO: 1; or
(b) a nucleotide sequence having an identity of 98% or more with the nucleotide sequence of SEQ ID NO 3.

9. The cDNA polynucleotide according to claim 4, consisting of the following nucleotide sequence:
(a) a nucleotide sequence having an identity of 99% or more with the nucleotide sequence of SEQ ID NO: 1; or
(b) a nucleotide sequence having an identity of 99% or more with the nucleotide sequence of SEQ ID NO 3.

10. A vector, comprising the cDNA polynucleotide according to claim 3.

11. A microbial cell, comprising the cDNA polynucleotide according to claim 3.

* * * * *

SEQUENCE LISTING

<160> NUMBER OF SEQ ID NOS: 8

<210> SEQ ID NO 1
<211> LENGTH: 1068
<212> TYPE: DNA
<213> ORGANISM: Plectospira myriandra
<220> FEATURE:
<223> OTHER INFORMATION: Polynucleotide encoding Omega-3 desaturase

<400> SEQUENCE: 1

```
atggtgtcga gtacaaaggg ggaaaaaccc gtcgaattcc caaccttgac ggaaattaaa      60
cattccattc ctaatacttg ctttgaatcg gatgcagcaa cttctctttta ctatgtgggt     120 cgttctggat tacttactgc tttgtttatg acgactttga gctatggtcg agctgccctt     180
gccgagtatt tcattttgga tgttcttctc tgtgctacgt atatttatct tcaaggcgtt     240
gtgttttggg gtcttttttac gattgggcat gattgtggtc acagttcgtt ttcgcgatat     300
catagcttga atttcattgt tggttgcatc actcattcag caattttaac tccatttgaa     360
```

-continued

```
agttggcgaa ttacgcatcg tcatcatcac aaaaatactg gaaatattga taaagatgaa    420
gtatttatc ctcaacgtga acaagatgcc tacacattaa ctcgtcaaat ggtctattcg     480
cttggatttg cttggtttac ataccttaaa gtgggttacg ttcctcgtca aatggatcac    540
tttaatcctt gggatcctct tctcgttcgt cgagcaggtg ctgtaattat ttccctttt    600
tgctggcttg ctatggtgct tggtttggcc tatcttactt acacacttgg tgttgccaca    660
atggcgttgt attattttgc tcctctcttt gtctttgcta cgttttggt catcacaacg     720
ttcttgcatc ataatgatga agatacacca tggtatggag actctgaatg gacgtatgtc    780
aaaggcaatc tttcatctgt ggatcgttca tatggatggc ttgttgatga attgagtcac    840
aatattggta ctcatcaaat tcatcatctc tttccgatca ttcctcacta caagctgaac    900
gaagcaacag cacatttcg taaagctttt cctgaatttg ttcgaaagaa tgatgaacca    960
attcttgctt cttttggaa aacaattcaa ctctttgtaa atcatggagt tgttccacaa   1020
gatgctcaaa tcttttcgtt gggtgaaagt gccaaaaaga cattgtaa              1068
```

<210> SEQ ID NO 2
<211> LENGTH: 355
<212> TYPE: PRT
<213> ORGANISM: Plectospira myriandra
<220> FEATURE:
<223> OTHER INFORMATION: Omega-3 desaturase

<400> SEQUENCE: 2

```
Met Val Ser Ser Thr Lys Gly Glu Lys Pro Val Glu Phe Pro Thr Leu
1               5                   10                  15

Thr Glu Ile Lys His Ser Ile Pro Asn Thr Cys Phe Glu Ser Asp Ala
            20                  25                  30

Ala Thr Ser Leu Tyr Tyr Val Gly Arg Ser Gly Leu Leu Thr Ala Leu
        35                  40                  45

Phe Met Thr Thr Leu Ser Tyr Gly Arg Ala Ala Leu Ala Glu Tyr Phe
    50                  55                  60

Ile Leu Asp Val Leu Leu Cys Ala Thr Tyr Ile Tyr Leu Gln Gly Val
65                  70                  75                  80

Val Phe Trp Gly Leu Phe Thr Ile Gly His Asp Cys Gly His Ser Ser
                85                  90                  95

Phe Ser Arg Tyr His Ser Leu Asn Phe Ile Val Gly Cys Ile Thr His
            100                 105                 110

Ser Ala Ile Leu Thr Pro Phe Glu Ser Trp Arg Ile Thr His Arg His
        115                 120                 125

His His Lys Asn Thr Gly Asn Ile Asp Lys Asp Glu Val Phe Tyr Pro
    130                 135                 140

Gln Arg Glu Gln Asp Ala Tyr Thr Leu Thr Arg Gln Met Val Tyr Ser
145                 150                 155                 160

Leu Gly Phe Ala Trp Phe Thr Tyr Leu Lys Val Gly Tyr Val Pro Arg
                165                 170                 175

Gln Met Asp His Phe Asn Pro Trp Asp Pro Leu Leu Val Arg Arg Ala
            180                 185                 190

Gly Ala Val Ile Ile Ser Leu Phe Cys Trp Leu Ala Met Val Leu Gly
        195                 200                 205

Leu Ala Tyr Leu Thr Tyr Thr Leu Gly Val Ala Thr Met Ala Leu Tyr
    210                 215                 220

Tyr Phe Ala Pro Leu Phe Val Phe Ala Thr Phe Leu Val Ile Thr Thr
225                 230                 235                 240
```

```
Phe Leu His His Asn Asp Glu Asp Thr Pro Trp Tyr Gly Asp Ser Glu
                245                 250                 255

Trp Thr Tyr Val Lys Gly Asn Leu Ser Ser Val Asp Arg Ser Tyr Gly
            260                 265                 270

Trp Leu Val Asp Glu Leu Ser His Asn Ile Gly Thr His Gln Ile His
        275                 280                 285

His Leu Phe Pro Ile Ile Pro His Tyr Lys Leu Asn Glu Ala Thr Ala
    290                 295                 300

His Phe Arg Lys Ala Phe Pro Glu Phe Val Arg Lys Asn Asp Glu Pro
305                 310                 315                 320

Ile Leu Ala Ser Phe Trp Lys Thr Ile Gln Leu Phe Val Asn His Gly
                325                 330                 335

Val Val Pro Gln Asp Ala Gln Ile Phe Ser Leu Gly Glu Ser Ala Lys
            340                 345                 350

Lys Thr Leu
        355

<210> SEQ ID NO 3
<211> LENGTH: 1068
<212> TYPE: DNA
<213> ORGANISM: Plectospira myriandra
<220> FEATURE:
<223> OTHER INFORMATION: Polynucleotide encoding Omega-3 desaturase

<400> SEQUENCE: 3
atggtgtcga gtacaaaggg ggaaaaacct gtcgaattcc caaccttgac tgaaatcaag      60
cattccattc ccaattcttg ctttgaatcg gatgcagcaa cttcgcttta ctatgtgggt     120
cgttctgcat tgcttactgc tttgtttatg acgactttga gccatggtcg agctgctctt     180
gccgattatt tcatttttgga tgttcttctc tgtgctacgt atatttatct tcaaggcgtt     240 gtgtttggg gtcttttttac gattggacat gactgtggac acagttcgtt ttcacgatat     300
catagcttga atttcattgt tggttgcatc actcattcag caattttaac tccatttgaa     360
agttggcgaa ttacgcatcg tcatcatcac aaaaatactg gaaatattga taaagatgaa     420
gtattttatc ctcaacgtga acaagacgcc tacacattaa ctcgtcaaat ggtgtattcg     480
cttggatttg cttggtttac ctaccttaaa gtgggttacg ttcctcgtca aatggaccac     540
ttcaatcctt gggatcctct tctcgttcgt cgagcaggtg ctgtaattat ttccctcttt     600
tgctggcttg ctatggtgct tggtttggct taccttactt atacacttgg tgttgccaca     660
atggcgttgt attattttgc tcctctcttt gtctttgcta cgttttttggt catcacgacg     720 ttcttgcatc ataatgatga agatacacca tggtatggag actctgaatg gacgtatgtc     780
aaaggcaatc tttcatctgt ggatcgttca tatggatggc ttgttgatga attgagtcac     840
aatattggta cacatcaaat tcatcatctc tttccaatca ttcctcacta caaactcaac     900
gaagcaacag cacattttcg taaagctttt cctgaatttg ttcgaaagaa tgatgaacca     960
attcttgctt cttttttggaa aacaattcaa ctctttgtaa atcatggagt tgttccacaa    1020
gatgctcaaa tcttttcgtt gggtgaaagt gccaaaaaga cattgtaa                 1068

<210> SEQ ID NO 4
<211> LENGTH: 355
<212> TYPE: PRT
<213> ORGANISM: Plectospira myriandra
<220> FEATURE:
<223> OTHER INFORMATION: Omega-3 desaturase
```

```
<400> SEQUENCE: 4

Met Val Ser Ser Thr Lys Gly Glu Lys Pro Val Glu Phe Pro Thr Leu
1               5                   10                  15

Thr Glu Ile Lys His Ser Ile Pro Asn Ser Cys Phe Glu Ser Asp Ala
            20                  25                  30

Ala Thr Ser Leu Tyr Tyr Val Gly Arg Ser Ala Leu Leu Thr Ala Leu
        35                  40                  45

Phe Met Thr Thr Leu Ser His Gly Arg Ala Ala Leu Ala Asp Tyr Phe
    50                  55                  60

Ile Leu Asp Val Leu Leu Cys Ala Thr Tyr Ile Tyr Leu Gln Gly Val
65                  70                  75                  80

Val Phe Trp Gly Leu Phe Thr Ile Gly His Asp Cys Gly His Ser Ser
                85                  90                  95

Phe Ser Arg Tyr His Ser Leu Asn Phe Ile Val Gly Cys Ile Thr His
            100                 105                 110

Ser Ala Ile Leu Thr Pro Phe Glu Ser Trp Arg Ile Thr His Arg His
        115                 120                 125

His His Lys Asn Thr Gly Asn Ile Asp Lys Asp Glu Val Phe Tyr Pro
    130                 135                 140

Gln Arg Glu Gln Asp Ala Tyr Thr Leu Thr Arg Gln Met Val Tyr Ser
145                 150                 155                 160

Leu Gly Phe Ala Trp Phe Thr Tyr Leu Lys Val Gly Tyr Val Pro Arg
                165                 170                 175

Gln Met Asp His Phe Asn Pro Trp Asp Pro Leu Leu Val Arg Arg Ala
            180                 185                 190

Gly Ala Val Ile Ile Ser Leu Phe Cys Trp Leu Ala Met Val Leu Gly
        195                 200                 205

Leu Ala Tyr Leu Thr Tyr Thr Leu Gly Val Ala Thr Met Ala Leu Tyr
    210                 215                 220

Tyr Phe Ala Pro Leu Phe Val Phe Ala Thr Phe Leu Val Ile Thr Thr
225                 230                 235                 240

Phe Leu His His Asn Asp Glu Asp Thr Pro Trp Tyr Gly Asp Ser Glu
                245                 250                 255

Trp Thr Tyr Val Lys Gly Asn Leu Ser Ser Val Asp Arg Ser Tyr Gly
            260                 265                 270

Trp Leu Val Asp Glu Leu Ser His Asn Ile Gly Thr His Gln Ile His
        275                 280                 285

His Leu Phe Pro Ile Ile Pro His Tyr Lys Leu Asn Glu Ala Thr Ala
    290                 295                 300

His Phe Arg Lys Ala Phe Pro Glu Phe Val Arg Lys Asn Asp Glu Pro
305                 310                 315                 320

Ile Leu Ala Ser Phe Trp Lys Thr Ile Gln Leu Phe Val Asn His Gly
                325                 330                 335

Val Val Pro Gln Asp Ala Gln Ile Phe Ser Leu Gly Glu Ser Ala Lys
            340                 345                 350

Lys Thr Leu
    355

<210> SEQ ID NO 5
<211> LENGTH: 1068
<212> TYPE: DNA
<213> ORGANISM: Plectospira myriandra
<220> FEATURE:
<223> OTHER INFORMATION: Polynucleotide encoding Omega-3 desaturase with
      codons optimized for expression in Mortierella alpina
```

<400> SEQUENCE: 5

```
atggtctcgt cgaccaaggg cgagaagccc gtcgagttcc ccaccctcac cgagatcaag      60
cactcgatcc ccaacacctg cttcgagtcg gacgctgcta cctcgctcta ctacgtcggt     120
cgctcgggtc tcctcaccgc cctcttcatg accaccctct cgtacggtcg cgctgctctg     180
gccgagtact tcatcctcga cgtcctcctc tgcgccacct acatctacct ccagggcgtc     240
gtcttctggg gcctcttcac catcggccac gactgcggcc actcgtcgtt ctcgcgctac     300
cactcgctca acttcatcgt cggctgcatc acccactcgg ccatcctcac ccccttcgag     360
tcgtggcgca tcacccaccg ccaccaccac aagaacaccg caacatcga caaggacgag     420
gtcttttacc ctcagcgcga gcaggacgcc tacaccctca cccgccagat ggtctactcg     480
ctcggcttcg cctggttcac ctacctcaag gtcggctacg ttcctcgcca gatgaccacc     540
ttcaacccct gggacccct cctcgtccgt cgtgctggcg ctgtcatcat ctcgctcttc     600
tgctggctcg ccatggtcct cggtttggcc tacctcacct acaccctcgg tgtcgccacc     660
atggccctct actacttcgc ccctctcttc gtcttcgcca ccttcctcgt catcaccacc     720
ttcctccacc acaacgacga ggacaccccc tggtacggcg actcggagtg gacctacgtc     780
aagggcaacc tctcgtcggt cgaccgctcg tacggctggc tcgtcgacga gctctcgcac     840
aacatcggca cccaccagat ccaccactc ttccccatca tccccactca agctcaac     900
gaggctaccg cccacttccg caaggccttc cccgagttcg tccgcaagaa cgacgagccc     960
atcctcgcct cgttctggaa gaccatccag ctcttcgtca ccacggcgt cgtccccag    1020
gacgcccaga tcttctcgct cggcgagtcg gccaagaaga ccctctaa                1068
```

<210> SEQ ID NO 6
<211> LENGTH: 1068
<212> TYPE: DNA
<213> ORGANISM: Plectospira myriandra
<220> FEATURE:
<223> OTHER INFORMATION: Polynucleotide encoding Omega-3 desaturase with codons optimized for expression in Mortierella alpina

<400> SEQUENCE: 6

```
atggtctcgt cgaccaaggg cgagaagccc gtcgagttcc ccaccctcac cgagatcaag      60
cactcgatcc ccaactcgtg cttcgagtcg gacgctgcta cctcgctcta ctacgtcggt     120
cgctcggctc tcctcaccgc cctcttcatg accaccctct cgcacggtcg cgctgctctg     180
gccgactact tcatcctcga cgtcctcctc tgcgccacct acatctacct ccagggcgtc     240
gtcttctggg gcctcttcac catcggccac gactgcggcc actcgtcgtt ctcgcgctac     300
cactcgctca acttcatcgt cggctgcatc acccactcgg ccatcctcac ccccttcgag     360
tcgtggcgca tcacccaccg ccaccaccac aagaacaccg caacatcga caaggacgag     420
gtcttttacc ctcagcgcga gcaggacgcc tacaccctca cccgccagat ggtctactcg     480
ctcggcttcg cctggttcac ctacctcaag gtcggctacg ttcctcgcca gatgaccacc     540
ttcaacccct gggacccct cctcgtccgt cgtgctggcg ctgtcatcat ctcgctcttc     600
tgctggctcg ccatggtcct cggtttggcc tacctcacct acaccctcgg tgtcgccacc     660
atggccctct actacttcgc ccctctcttc gtcttcgcca ccttcctcgt catcaccacc     720
ttcctccacc acaacgacga ggacaccccc tggtacggcg actcggagtg gacctacgtc     780
aagggcaacc tctcgtcggt cgaccgctcg tacggctggc tcgtcgacga gctctcgcac     840
aacatcggca cccaccagat ccaccactc ttccccatca tccccactca agctcaac     900
```

-continued

```
gaggctaccg cccacttccg caaggccttc cccgagttcg tccgcaagaa cgacgagccc      960
atcctcgcct cgttctggaa gaccatccag ctcttcgtca accacggcgt cgtccccag      1020 gacgcccaga tcttctcgct cggcgagtcg gccaagaaga ccctctaa                  1068

<210> SEQ ID NO 7
<211> LENGTH: 28
<212> TYPE: DNA
<213> ORGANISM: Artificial sequence
<220> FEATURE:
<223> OTHER INFORMATION: Oligonucleotide as PCR primer

<400> SEQUENCE: 7
gaaatggccg acgtgaacac ctcctcgc                                          28

<210> SEQ ID NO 8
<211> LENGTH: 26
<212> TYPE: DNA
<213> ORGANISM: Artificial sequence
<220> FEATURE:
<223> OTHER INFORMATION: Oligonucleotide as PCR primer

<400> SEQUENCE: 8
ctatgcgcgc ttggtgagca cctcgc                                            26
```